(12) United States Patent
Takeuchi et al.

(10) Patent No.: US 10,215,770 B2
(45) Date of Patent: Feb. 26, 2019

(54) AUTOMATIC ANALYZER

(71) Applicant: Toshiba Medical Systems Corporation, Otawara-shi (JP)

(72) Inventors: Michiaki Takeuchi, Otawara (JP); Tomomi Muramatsu, Otawara (JP); Masahiro Masubuchi, Yaita (JP); Satoshi Matsumoto, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/702,464

(22) Filed: Sep. 12, 2017

(65) Prior Publication Data

US 2018/0003727 A1 Jan. 4, 2018

Related U.S. Application Data

(62) Division of application No. 14/601,757, filed on Jan. 21, 2015.

(30) Foreign Application Priority Data

Jan. 31, 2014 (JP) .................................. 2014-017459

(51) Int. Cl.
*G01N 35/00* (2006.01)
*G01N 15/06* (2006.01)
(Continued)

(52) U.S. Cl.
CPC ..... *G01N 35/0098* (2013.01); *G01N 15/0606* (2013.01); *G01N 15/0656* (2013.01); *G01N 33/5302* (2013.01); *G01N 35/025* (2013.01); *G01N 35/1002* (2013.01); *G01N 2015/0693* (2013.01); *G01N 2035/00356* (2013.01);
(Continued)

(58) Field of Classification Search
None
See application file for complete search history.

(56) References Cited

U.S. PATENT DOCUMENTS

| 5,302,347 A | 4/1994 | Van Den Berg |
| 2003/0059823 A1 | 3/2003 | Matsunaga |
| 2010/0062433 A1 | 3/2010 | Nagaoka |

FOREIGN PATENT DOCUMENTS

| JP | 2003-93039 A | 4/2003 |
| JP | 2007-47027 A | 2/2007 |

(Continued)

OTHER PUBLICATIONS

Japanese Office Action dated Oct. 31, 2017 in Japanese Patent Application No. 2014-017459.

*Primary Examiner* — Kathryn Wright
(74) *Attorney, Agent, or Firm* — Oblon, McClelland, Maier & Neustadt, L.L.P.

(57) ABSTRACT

According to one embodiment, an automatic analyzer includes dispenser, measurer, thermostat, cooler and cleaner. Dispenser dispenses a specimen and a reagent into a reaction vessel. Measurer measures a solution mixture of the specimen and the reagent in the vessel. Thermostat heats the mixture to a first temperature at which thermoresponsive polymers contained in the reagent aggregate. Cooler cools a cleaning fluid used to clean the vessel to a second temperature lower than the first temperature, at which the polymers contained in the reagent disperse. Cleaner cleans the vessel from which the mixture has been drained, using the cooled fluid.

7 Claims, 9 Drawing Sheets

(51) Int. Cl.
  *G01N 35/10* (2006.01)
  *G01N 33/53* (2006.01)
  *G01N 35/02* (2006.01)

(52) U.S. Cl.
  CPC .............. *G01N 2035/00396* (2013.01); *G01N 2035/00445* (2013.01); *G01N 2035/00564* (2013.01); *G01N 2035/1048* (2013.01)

(56) References Cited

FOREIGN PATENT DOCUMENTS

| | | |
|---|---|---|
| JP | 2009-168636 | 7/2009 |
| JP | 2011-99807 A | 5/2011 |

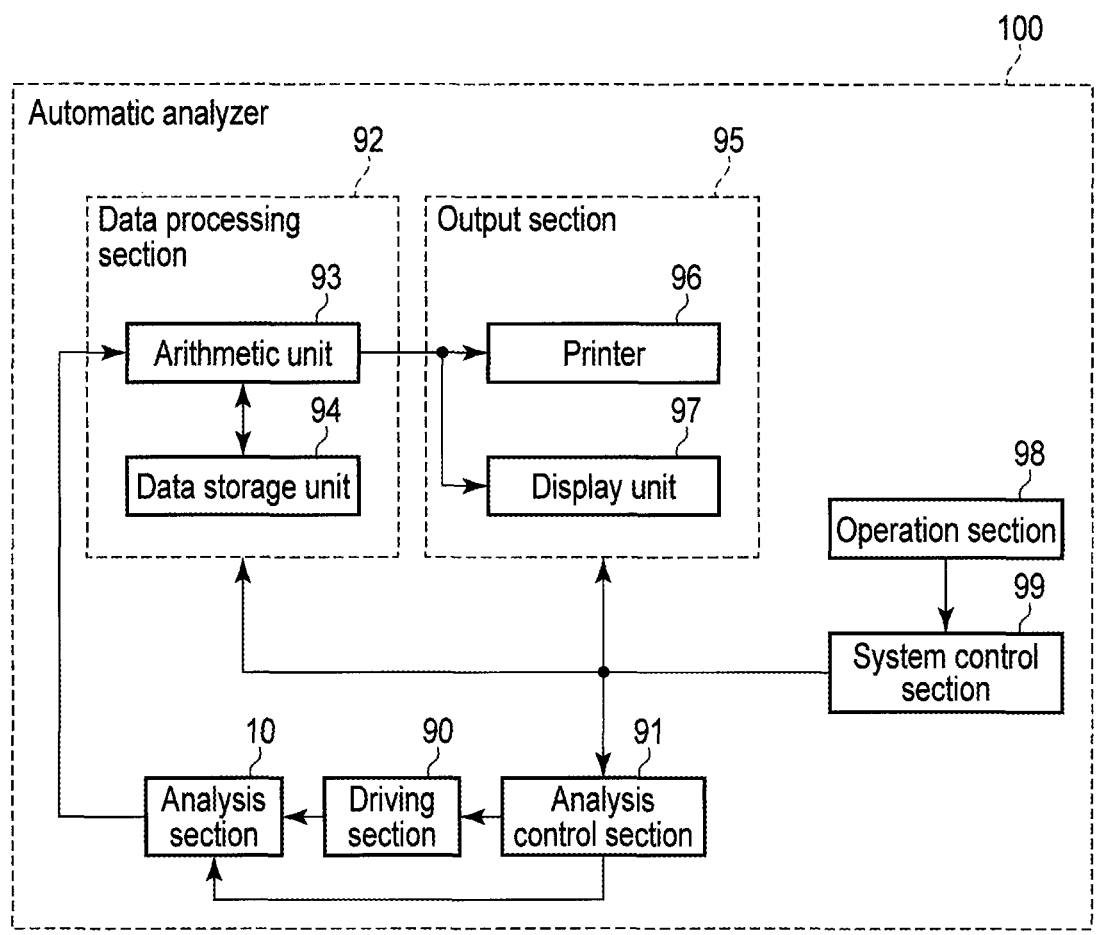
F I G. 1

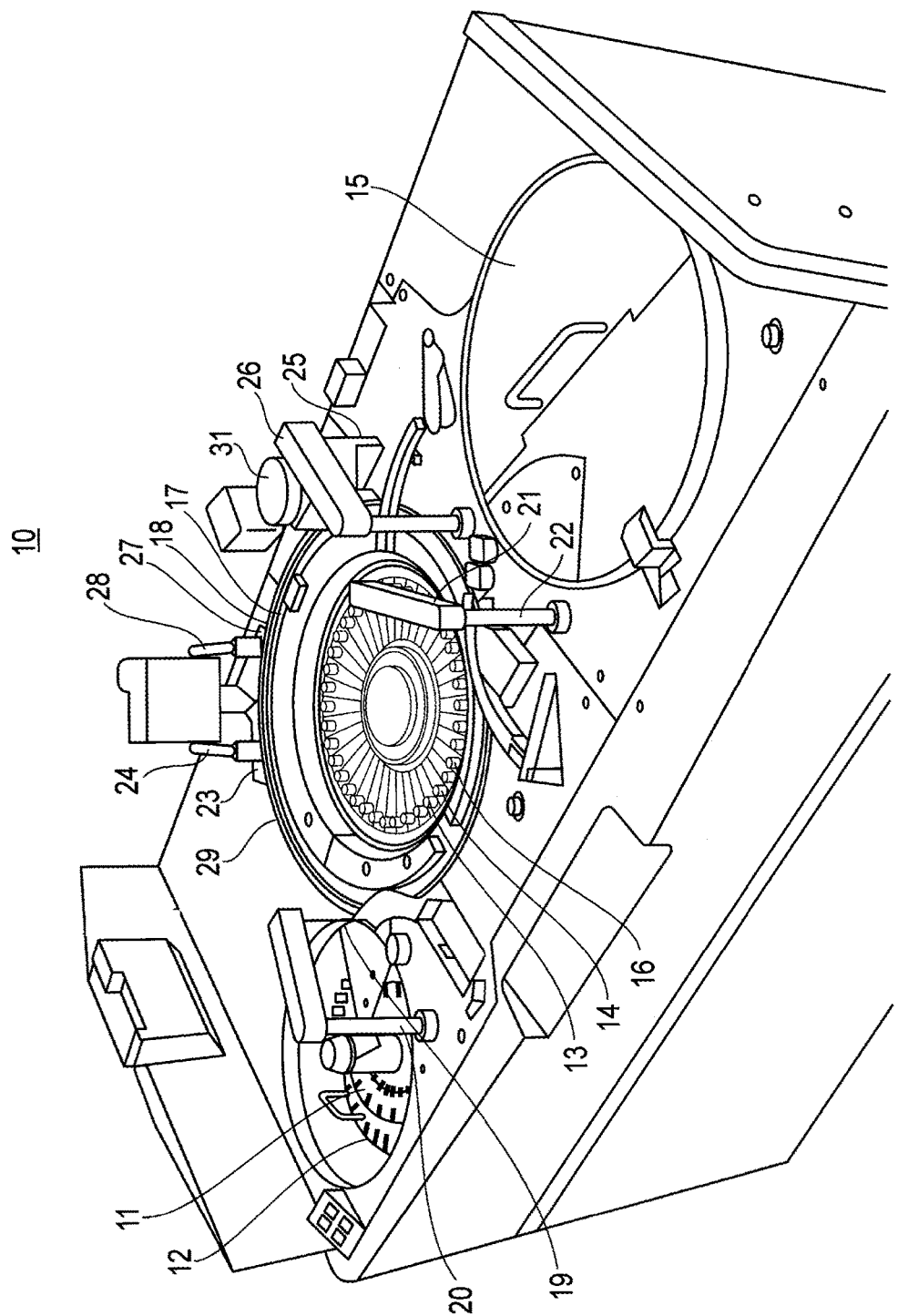
F I G. 2

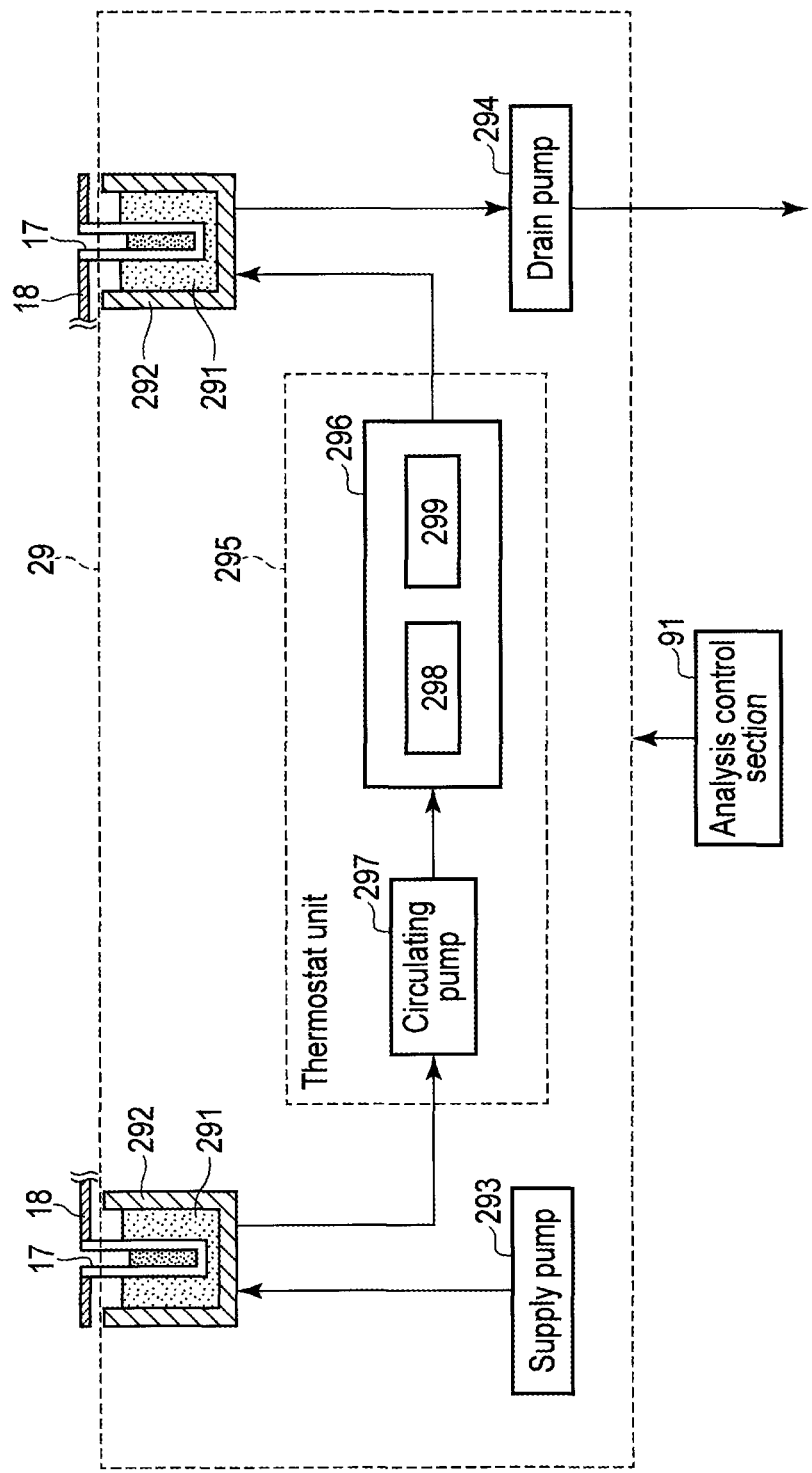
F I G. 5

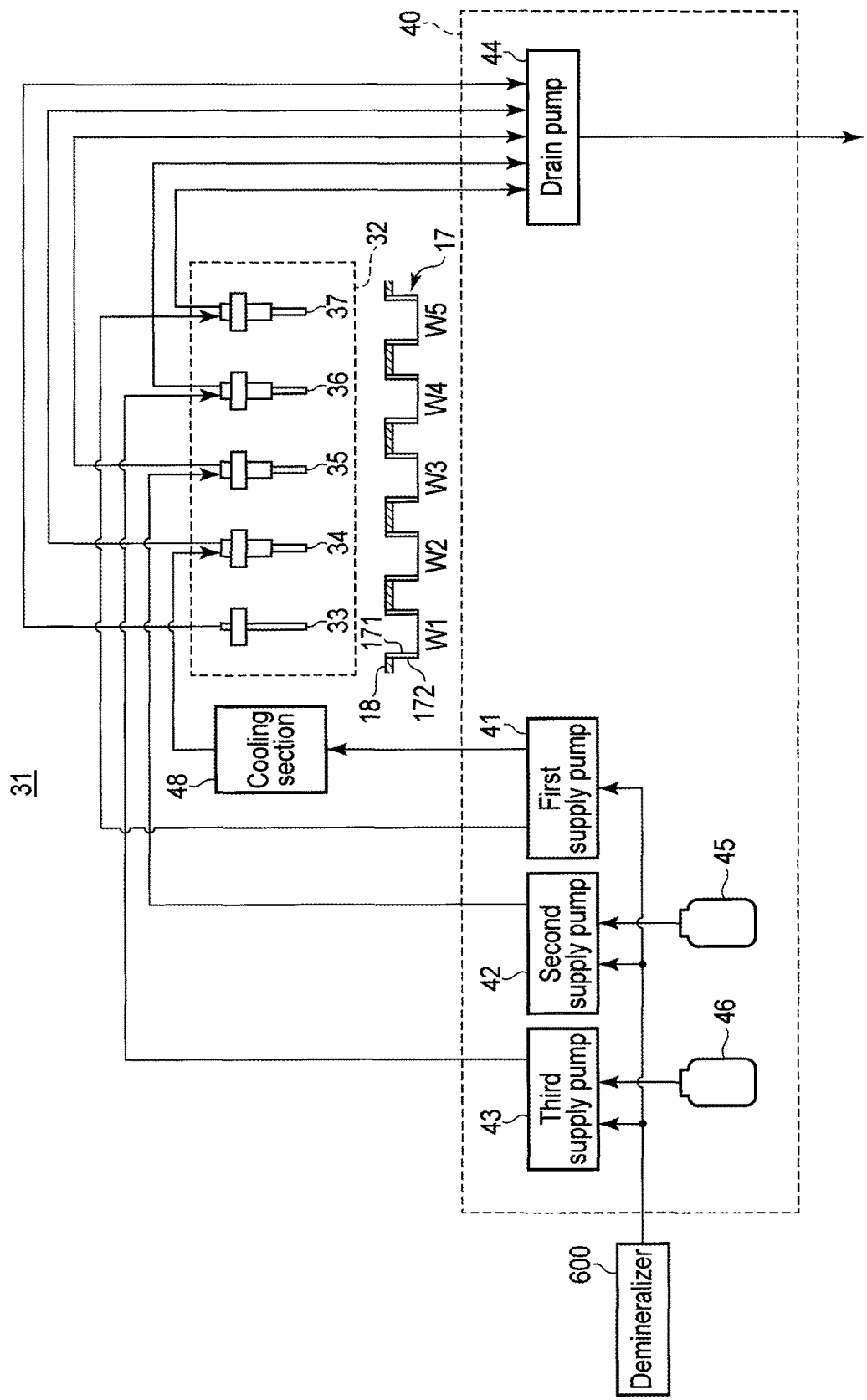
F I G. 6

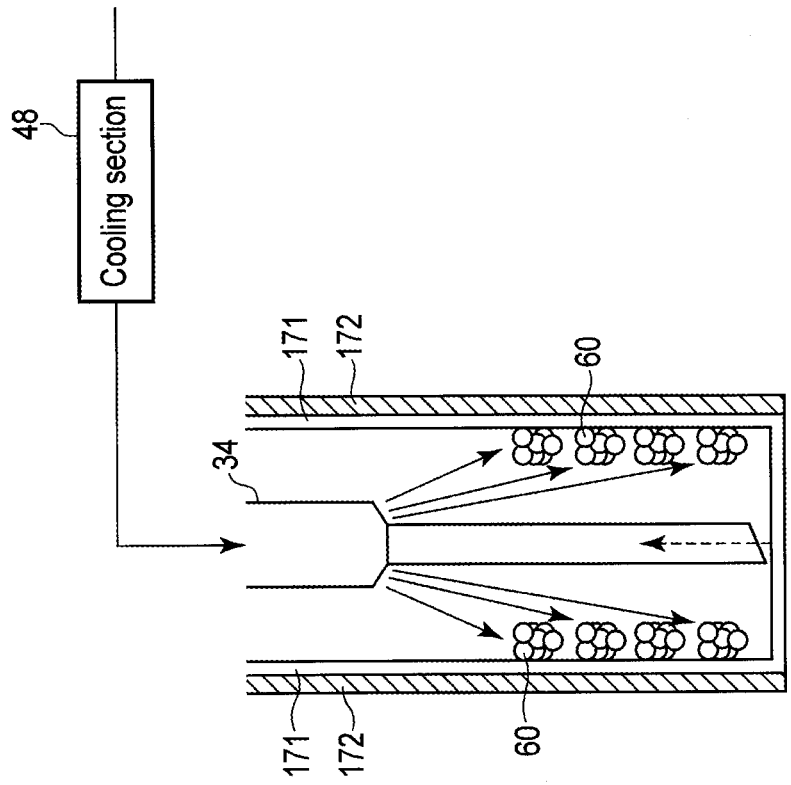
F I G. 10B
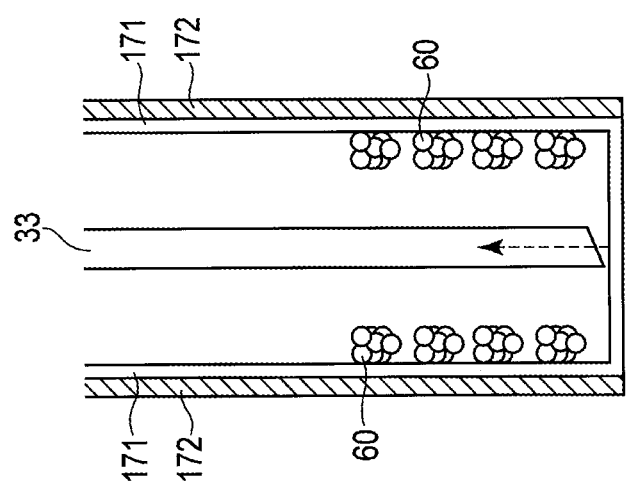
F I G. 10A

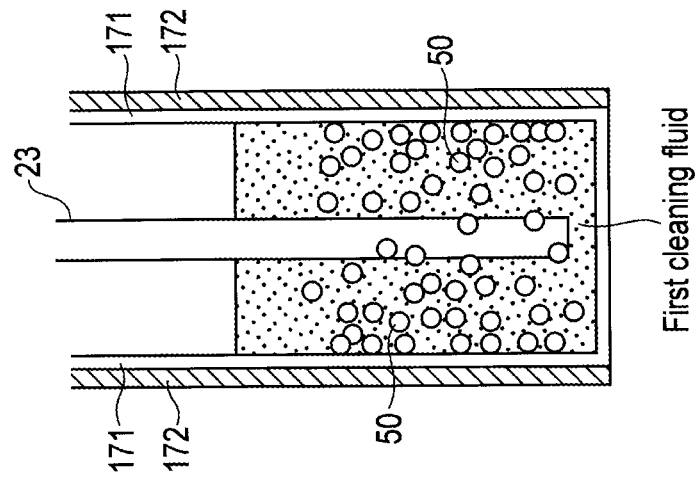
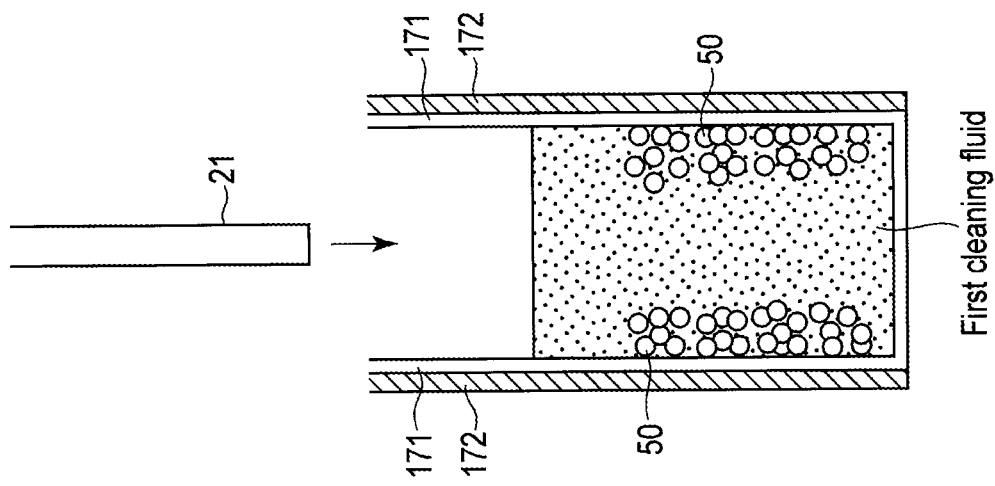

AUTOMATIC ANALYZER

CROSS-REFERENCE TO RELATED APPLICATIONS

This application is a divisional of U.S. application Ser. No. 14/601,757 filed Jan. 21, 2015 and is based upon and claims the benefit of priority from the Japanese patent application Ser. No. 2014-017459, filed Jan. 31, 2014, the entire contents of each of which are incorporated herein by reference.

FIELD

Embodiments described herein relate generally to an automatic analyzer.

BACKGROUND

An automatic analyzer is used to automate a biochemical inspection, an immunoassay, and the like. The automatic analyzer mixes a reagent prepared for each inspection item with a specimen in a reaction vessel and causes them to react. In the automatic analyzer, a measuring section optically measures turbidity or a change in the tone caused in the solution mixture by the reaction. Analysis data represented by the concentration of each inspection item component included in the specimen, the activity of an enzyme, and the like is thus generated.

The immunoassay is done by measuring a change in turbidity of a solution mixture. The turbidity is caused by an aggregation that occurs due to the reaction between an antibody in a reagent and an antigen in a specimen. The turbidity is also caused by an aggregation that occurs due to the reaction between an antibody immobilized to a latex particle in a reagent and an antigen in a specimen.

A method using a reagent containing magnetic particles is also usable. In this method, an aggregate formed by the reaction between an antibody immobilized to a magnetic particle in a reagent and an antigen in a specimen is attracted by a magnet to the inner surfaces (two opposite surfaces) of a reaction vessel, and a change in turbidity of the solution mixture is then measured. That is, the aggregate is magnetically separated from other substances in the solution mixture (magnetic separation).

However, the magnetically separated aggregates readily remain on the inner surfaces of the reaction vessel as a contaminant. Since the reaction vessel is repetitively cleaned and reused for the next measurement, the residual aggregates adversely affect the next measurement.

BRIEF DESCRIPTION OF THE DRAWINGS

FIG. 1 is a block diagram showing an example of an automatic analyzer according to an embodiment;

FIG. 2 is a perspective view showing an example of an analysis section according to the embodiment;

FIG. 5 is a view showing an example of a thermostat section according to the embodiment;

FIG. 6 is a view showing an example of a cleaning section according to the embodiment;

FIG. 10A is a view showing the state in the reaction vessel cleaned by a first cleaning nozzle according to the embodiment;

FIG. 10B is a view showing the state in the reaction vessel cleaned by a second cleaning nozzle according to the embodiment;

FIG. 11A is a view showing the state in the reaction vessel cleaned by a first reagent dispensing probe according to the embodiment; and FIG. 11B is a view showing the state in the reaction vessel cleaned by a first stirrer according to the embodiment.

DETAILED DESCRIPTION

Figure 3:
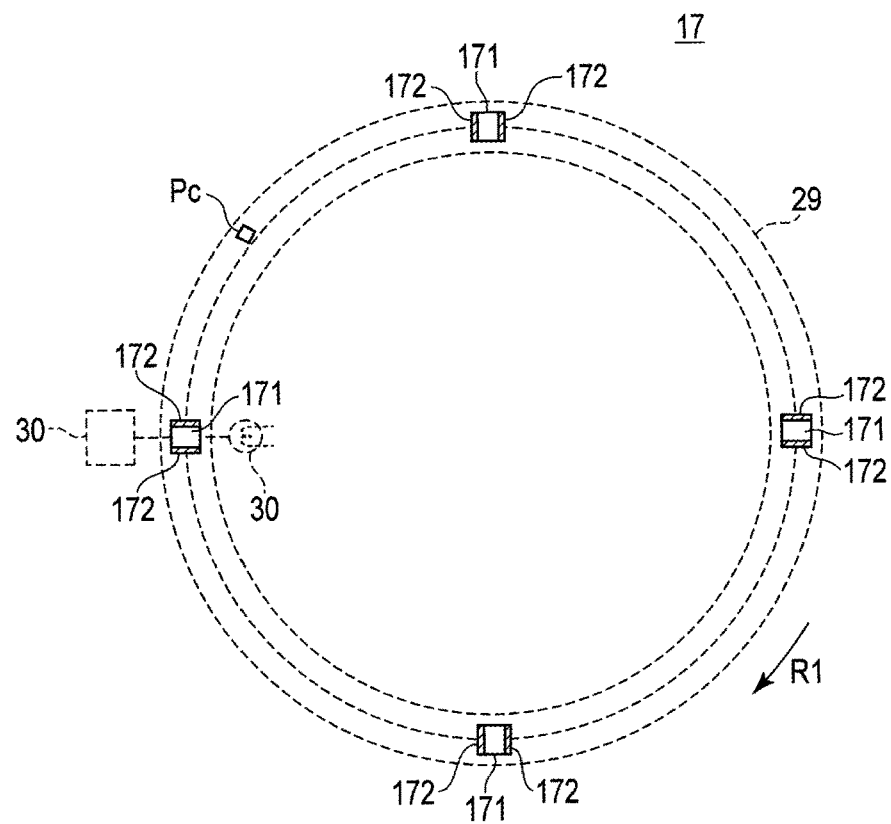
FIG. 3 is a plan view of a reaction section according to the embodiment.

In general, according to one embodiment, an automatic analyzer includes a dispenser, a measurement unit, a thermostat unit, a cooler and a cleaner. The dispenser dispenses a specimen and a reagent into a reaction vessel. The measurement unit measures a solution mixture of the specimen and the reagent in the reaction vessel. The thermostat unit heats the solution mixture to a first temperature at which thermoresponsive polymers contained in the reagent aggregate. The cooler cools a cleaning fluid used to clean the reaction vessel to a second temperature lower than the first temperature, at which the thermoresponsive polymers contained in the reagent disperse. The cleaner cleans the reaction vessel from which the solution mixture has been drained, using the cleaning fluid cooled to the second temperature.

An embodiment will now be described with reference to the accompanying drawings.

FIG. 1 is a block diagram showing an example of an automatic analyzer according to the embodiment. An automatic analyzer 100 includes an analysis section 10, a driving section 90, and an analysis control section 91. The analysis section 10 measures the solution mixture of the reagent and the standard specimen of each inspection item or the solution mixture of a test specimen and the reagent of each inspection item and generates standard data or test data. The driving section 90 drives analysis units concerning the measurement of the analysis section 10. The analysis control section 91 controls the driving section 90.

The automatic analyzer 100 also includes a data processing section 92, an output section 95, an operation section 98, and a system control section 99. The data processing section 92 outputs calibration data or analysis data based on the standard data or test data generated by the analysis section 10. The output section 95 prints or displays the calibration data or analysis data generated by the data processing section 92. The operation section 98 is used to, for example, do input to set the analysis parameters of each inspection item. The system control section 99 controls the analysis control section 91, the data processing section 92, and the output section 95.

FIG. 2 is a perspective view showing an example of the analysis section 10 shown in FIG. 1. The analysis section 10 includes a specimen container 11 and a sample table 12. The specimen container 11 stores a specimen such as the standard specimen of each inspection item or a test specimen. The sample table 12 movably holds the specimen container 11.

The analysis section 10 further includes reagent containers 13, a first reagent storage 15, and a second reagent storage 16. The reagent containers 13 store a first reagent and a second reagent of each inspection item. The first reagent storage 15 keeps the first reagent in the reagent containers 13 at a cold temperature Tr (for example, 2° C. to 10° C.) lower than the room temperature in the installation environment of the automatic analyzer 100. The second reagent storage 16 keeps the second reagent in the reagent containers 13 at the cold temperature Tr.

A reagent rack 14 is arranged in the first reagent storage 15. The reagent rack 14 movably holds the reagent containers 13. The reagent rack 14 is arranged in the second reagent storage 16 as well. For example, in the second reagent storage 16, a reaction section 17 is arranged on the circumference. The reaction section 17 is rotatably held by a reaction table 18.

The analysis section 10 also includes a sample dispensing probe 19 and a sample dispensing arm 20. The sample dispensing probe 19 sucks up the specimen in the specimen container 11 held by the sample table 12, and discharges (dispenses) it to the reaction section 17. The sample dispensing arm 20 pivotally and vertical-movably holds the sample dispensing probe 19.

The analysis section 10 further includes a first reagent dispensing probe 21 and a first reagent dispensing arm 22. The first reagent dispensing probe 21 sucks up the first reagent in the reagent container 13 held by the reagent rack 14 in the first reagent storage 15, and discharges (dispenses) it to the reaction section 17 in which the specimen already exists. The first reagent dispensing arm 22 pivotally and vertical-movably holds the first reagent dispensing probe 21.

The analysis section 10 also includes a first stirrer 23 and a first stirring arm 24. The first stirrer 23 stirs the solution mixture in the reaction section 17 to evenly mix the specimen and the first reagent. The first stirring arm 24 pivotally and vertical-movably holds the first stirrer 23.

The analysis section 10 further includes a second reagent dispensing probe 25 and a second reagent dispensing arm 26. The second reagent dispensing probe 25 sucks up the second reagent in the reagent container 13 held by the reagent rack 14 in the second reagent storage 16, and discharges (dispenses) it to the reaction section 17 in which the solution mixture of the specimen and the first reagent already exists. The second reagent dispensing arm 26 pivotally and vertical-movably holds the second reagent dispensing probe 25.

The analysis section 10 also includes a second stirrer 27 and a second stirring arm 28. The second stirrer 27 further stirs the solution mixture in the reaction section 17 to evenly mix the specimen, the first reagent, and the second reagent. The second stirring arm 28 pivotally and vertical-movably holds the second stirrer 27.

The analysis section 10 also includes a thermostat section 29, a measuring section 30, and a cleaning section 31. The thermostat section 29 heats the solution mixture in the reaction section 17. The measuring section 30 optically measures the characteristic of the heated solution mixture by irradiating the reaction section 17 with light. The cleaning section 31 cleans the reaction section 17 after the measurement by the measuring section 30.

The measuring section 30 includes a light source and a detector that detects light from the light source. When the rotatably moving reaction section 17 has arrived at the measurement position, the measuring section 30 irradiates it with light. Then, the light (transmitted light) that has passed through the solution mixture (containing the standard specimen) in the reaction section 17 exits from the side (exit end) opposite to the incident end. The detector provided near the exit end detects the transmitted light and outputs an electrical signal. Standard data is generated based on the electrical signal.

In a similar manner, the solution mixture including the test specimen in the reaction section 17 is also irradiated with light. The detector detects the transmitted light from the reaction section 17 and generates test data. The generated standard data and test data are output to the data processing section 92.

The driving section 90 shown in FIG. 1 includes a mechanism that drives the analysis units of the analysis section 10. The driving section 90 drives the sample table 12 to move the specimen container 11. The driving section 90 drives each reagent rack 14 to pivot the reagent containers 13. The driving section 90 drives the reaction table 18 to rotate the reaction section 17.

The driving section 90 pivotally and vertically drives the sample dispensing arm 20 to move the sample dispensing probe 19. The driving section 90 pivotally and vertically drives the first reagent dispensing arm 22 to move the first reagent dispensing probe 21. The driving section 90 pivotally and vertically drives the first stirring arm 24 to move the first stirrer 23. The driving section 90 pivotally and vertically drives the second reagent dispensing arm 26 to move the second reagent dispensing probe 25. The driving section 90 pivotally and vertically drives the second stirring arm 28 to move the second stirrer 27. The driving section 90 vertically moves part of the cleaning section 31.

The data processing section 92 includes an arithmetic unit 93 and a data storage unit 94. The arithmetic unit 93 processes standard data or test data generated by the measuring section 30 of the analysis section 10 and generates calibration data or analysis data of each inspection item. The data storage unit 94 stores the calibration data or analysis data generated by the arithmetic unit 93.

The arithmetic unit 93 generates calibration data of each inspection item based on the standard data generated by the measuring section 30 and a standard value preset for a standard specimen. The arithmetic unit 93 generates analysis data represented as a concentration value or the activity of an enzyme based on the test data generated by the measuring section 30 and calibration data of the inspection item corresponding to the test data.

The data storage unit 94 includes a memory device such as a hard disk. The data storage unit 94 stores the calibration data generated by the arithmetic unit 93 on an inspection item basis. The data storage unit 94 stores the analysis data of each inspection item generated by the arithmetic unit 93 on a test specimen basis.

The output section 95 includes a printer 96 and a display unit 97. The printer 96 includes a printer or the like, and prints the calibration data or analysis data output from the arithmetic unit 93 on print paper or the like in accordance with a preset format. The display unit 97 displays the calibration data or analysis data output from the arithmetic unit 93 of the data processing section 92.

The display unit 97 includes a monitor such as a CRT or a liquid crystal panel, and displays the calibration data or analysis data generated by the arithmetic unit 93 on the monitor. The display unit 97 displays an analysis parameter setting window and an inspection item setting window on the monitor. The analysis parameter setting window is used to set analysis parameters on an inspection item basis. The inspection item setting window is used to set identification information such as a name or ID for identifying a test specimen and an inspection item on an inspection item basis.

The operation section 98 includes an input device such as a keyboard, a mouse, a button, or a touch key panel. Using the operation section 98, the user sets the analysis parameters of each inspection item, inputs the identification information of a test specimen to be inspected to the system, or sets an inspection item for the test specimen to be inspected.

The system control section 99 includes a CPU and a memory. The system control section 99 stores the information input from the operation section 98, including the analysis parameters of each inspection item, the identification information of the test specimen to be inspected, and the inspection item. The system control section 99 generally controls the analysis control section 91, the data processing section 92, and the output section 95 based on these pieces of input information, thereby controlling the entire system.

Details of the arrangement of the reaction section 17, the thermostat section 29, and the cleaning section 31 in the analysis section 10 will be described next.

FIG. 3 is a plan view of the reaction section 17. The reaction section 17 includes a plurality of reaction vessels 171 arranged in the thermostat section 29. The reaction vessels 171 are arrayed on the circumference at, for example, equal intervals. The reaction vessels 171 have, for example, a quadrangular columnar shape having four side surfaces (side walls). Each reaction vessel 171 includes two (a pair of) magnets 172 arranged on two side surfaces viewed from the center of the circle. Each reaction vessel 171 is rotated by the driving section 90 in the direction of an arrow R1.

Figure 4:
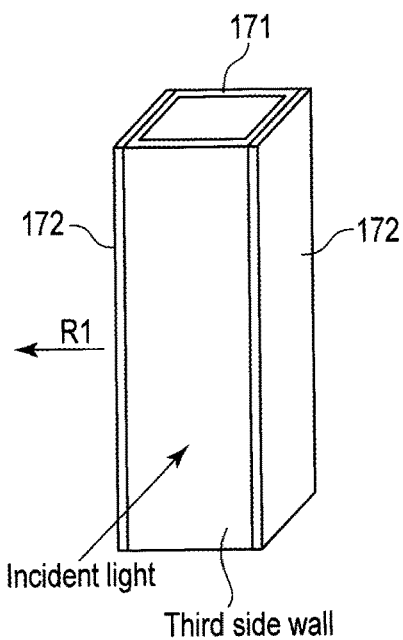
FIG. 4 is a perspective view showing an example of the arrangement of a reaction vessel and magnets according to the embodiment.

FIG. 4 is a perspective view showing an example of the arrangement of the reaction vessel 171 and the magnets 172. The reaction vessel 171 is formed into a quadrangular columnar shape. The reaction vessel 171 includes a first side wall, a second side wall, a third side wall, and a fourth side wall which form the side portions, and an opening formed on the upper side. The magnets 172 are formed into a plate shape. The magnets 172 are arranged on the outer surfaces of the first side wall and the second side wall perpendicular to the direction R1 that is the traveling direction of the reaction vessel 171.

Incident light that has entered from the outer surface of the third side wall perpendicular to the first side wall and the second side wall passes through the solution mixture and exits from the outer surface of the fourth side wall facing the third side wall. Note that the magnets 172 may be attached to the outer surfaces of the third side wall and the fourth side wall. In this arrangement, a through hole may be formed to make the light from the measuring section 30 located on the outer surface of the third side wall enter to and exit from the reaction vessel 171.

FIG. 5 is a view showing an example of the thermostat section 29. The thermostat section 29 includes a heating medium 291 and a constant temperature oven 292. The heating medium 291 transmits heat to heat the solution mixture in the reaction vessel 171 of the reaction section 17 to a measurement temperature Tm. The constant temperature oven 292 stores the reaction section 17 and the heating medium 291.

The thermostat section 29 also includes a supply pump 293 and a drain pump 294. The supply pump 293 supplies the heating medium 291 to the constant temperature oven 292. The drain pump 294 drains the heating medium 291 from the constant temperature oven 292.

The thermostat section 29 further includes a heater 295. The heater 295 heats the heating medium 291 supplied to the constant temperature oven 292, thereby heating the solution mixture in the reaction vessel 171 to the measurement temperature Tm (for example, 37 degree Celsius) higher than the room temperature.

In the constant temperature oven 292, a circular channel opening upward is formed along the circular track of the reaction section 17 that rotates. The reaction section 17 is arranged in the channel.

The heater 295 also includes a heating device 296 and a circulating pump 297. The heating device 296 heats the heating medium 291. The circulating pump 297 circulates the heating medium 291 between the constant temperature oven 292 and the heating device 296. The solution mixture in the reaction vessel 171 is heated to the measurement temperature Tm under the control of the analysis control section 91.

The heating device 296 includes a heater 298 and a temperature sensor 299. The temperature sensor 299 detects the temperature of the heating medium 291 in the heating device 296 and outputs a detection signal to the analysis control section 91. The analysis control section 91 heats the heater 298 based on the detection signal from the temperature sensor 299 and holds the heating medium 291 at the measurement temperature Tm. The circulating pump 297 sucks the heating medium 291 in the constant temperature oven 292, and supplies the heating medium 291 to the constant temperature oven 292 via the heating device 296.

Note that the plate-shaped magnets 172 arranged on the reaction vessel 171 of the reaction section 17 can be replaced with an annular magnet. The annular magnet can be arranged on at least one of the outer side surface and the inner side surface, which form the channel in the constant temperature oven 292, near at least one of the third side wall outer surface and the fourth side wall outer surface of each reaction vessel 171.

FIG. 6 is a view showing an example of the cleaning section 31 according to the embodiment. The cleaning section 31 includes a cleaning nozzle 32, a supply section 40, and a cooling section 48. The cleaning nozzle 32 cleans the interior of each reaction vessel 171 of the reaction section 17. The supply section 40 supplies, to the cleaning nozzle 32, a cleaning fluid to clean the reaction vessels 171. The cooling section 48 cools the cleaning fluid to be supplied to the cleaning nozzle 32.

The cleaning nozzle 32 includes, for example, a first cleaning nozzle 33, a second cleaning nozzle 34, a third cleaning nozzle 35, a fourth cleaning nozzle 36, and a fifth cleaning nozzle 37. The first cleaning nozzle 33, the second cleaning nozzle 34, the third cleaning nozzle 35, the fourth cleaning nozzle 36, and the fifth cleaning nozzle 37 clean the reaction vessel 171 that has undergone the measurement in the measuring section 30 of the analysis section 10.

The first cleaning nozzle 33 sucks the solution mixture in the reaction vessel 171 that has undergone the measurement in the measuring section 30 of the analysis section 10 and stopped at a first cleaning position W1 by the suction operation of the supply section 40 and cleans the reaction vessel 171.

The second cleaning nozzle 34, the third cleaning nozzle 35, the fourth cleaning nozzle 36, and the fifth cleaning nozzle 37 clean the reaction vessel 171 using cleaning fluids by the series of operations including the supply operation of the supply section 40 and the suction operation following the supply operation.

After the solution mixture is drained at the first cleaning position W1, the second cleaning nozzle 34 cleans the reaction vessel 171 that has stopped at a second cleaning position W2 using a first cleaning fluid (for example, ion exchanged water or distilled water) cooled by the cooling section 48. Here, assume that the first cleaning fluid is discharged into the reaction vessel 171 and then sucked from the reaction vessel 171.

The third cleaning nozzle 35 discharges and sucks a second cleaning fluid (for example, alkaline cleaning fluid) into and from the reaction vessel 171 that has stopped at a third cleaning position W3 after the stop at the second cleaning position W2, thereby cleaning the reaction vessel 171.

The fourth cleaning nozzle 36 discharges and sucks a third cleaning fluid (for example, acid cleaning fluid) into and from the reaction vessel 171 that has stopped at a fourth cleaning position W4 after the stop at the third cleaning position W3, thereby cleaning the reaction vessel 171.

The fifth cleaning nozzle 37 discharges and sucks the first cleaning fluid into and from the reaction vessel 171 that has stopped at a fifth cleaning position W5 after the stop at the fourth cleaning position W4, thereby cleaning the reaction vessel 171.

The supply section 40 includes a first supply pump 41 and a second supply pump 42. The first supply pump 41 supplies the first cleaning fluid to the second cleaning nozzle 34 and the fifth cleaning nozzle 37 of the cleaning nozzle 32. The second supply pump 42 supplies the second cleaning fluid to the third cleaning nozzle 35.

The supply section 40 includes a third supply pump 43 and a drain pump 44. The third supply pump 43 supplies the third cleaning fluid to the fourth cleaning nozzle 36. The drain pump 44 causes the first to fifth cleaning nozzles 33 to 37 to suck the solution mixture and the first to third cleaning fluids and drains them to the outside.

The supply section 40 includes a first container 45 that stores the stock solution of the second cleaning fluid, and a second container 46 that stores the stock solution of the third cleaning fluid.

The first supply pump 41 sucks rinse water from a demineralizer 600, and supplies the sucked rinse water to the second cleaning nozzle 34 as the first cleaning fluid cooled by the cooling section 48. The first supply pump 41 sucks the rinse water from the demineralizer 600, and supplies the sucked rinse water to the fifth cleaning nozzle 37 as the first cleaning fluid.

The second supply pump 42 sucks the rinse water from the demineralizer 600 and the stock solution of the second cleaning fluid from the first container 45. The second supply pump 42 dilutes the stock solution of the second cleaning fluid with the sucked rinse water at a predetermined factor, and supplies the diluted second cleaning fluid to the third cleaning nozzle 35.

The third supply pump 43 sucks the rinse water from the demineralizer 600 and the stock solution of the third cleaning fluid from the second container 46. The third supply pump 43 dilutes the stock solution of the third cleaning fluid with the sucked rinse water at a predetermined factor, and supplies the diluted third cleaning fluid to the fourth cleaning nozzle 36.

The drain pump 44 causes the first cleaning nozzle 33 to suck the solution mixture in the reaction vessel 171 by the suction operation. The drain pump 44 causes the second cleaning nozzle 34 and the fifth cleaning nozzle 37 to suck the first cleaning fluid in the reaction vessel 171. The drain pump 44 causes the third cleaning nozzle 35 to suck the second cleaning fluid in the reaction vessel 171. The drain pump 44 causes the fourth cleaning nozzle 36 to suck the third cleaning fluid in the reaction vessel 171.

The cooling section 48 includes a cooler (for example, Peltier element) and a tube arranged close to the cooler. The cooling section 48 causes the cooler to cool the first cleaning fluid, which has flowed into the tube by the supply operation of the first supply pump 41 of the supply section 40, to a cleaning temperature Tw (for example, 2 to 10 degree Celsius) lower than the room temperature. The cooled first cleaning fluid is supplied to the second cleaning nozzle 34 by the next supply operation of the first supply pump 41.

Components included in the reagent of an inspection item A1 used to analyze a target substance A and the reaction between the components and the target substance A will be described next.

Figure 7:
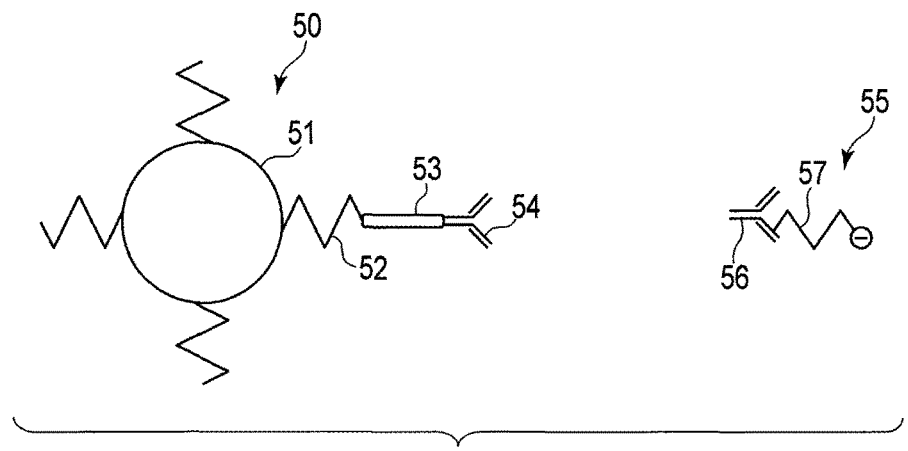
FIG. 7 is a view showing an example of components contained in the reagent of an inspection item according to the embodiment.

FIG. 7 is a view showing an example of components included in the reagent of the inspection item A1. The reagent of the inspection item A1 is a two-reagent system including, for example, a first reagent and a second reagent paired with the first reagent. The second reagent includes a primary reactant 50 and a secondary reactant 55, which specifically react with and bind to the target substance A that is, for example, an antigen.

The primary reactant 50 contains a magnetic particle 51 and thermoresponsive polymers 52 immobilized to the surface of the magnetic particle 51. The thermoresponsive polymers 52 aggregate and disperse in response to heat. The primary reactant 50 contains a first antibody 54. The first antibody 54 binds to the magnetic particle 51 and the thermoresponsive polymer 52 via a cross-linking body 53, and reacts with and binds to the target substance A.

Figure 8A:
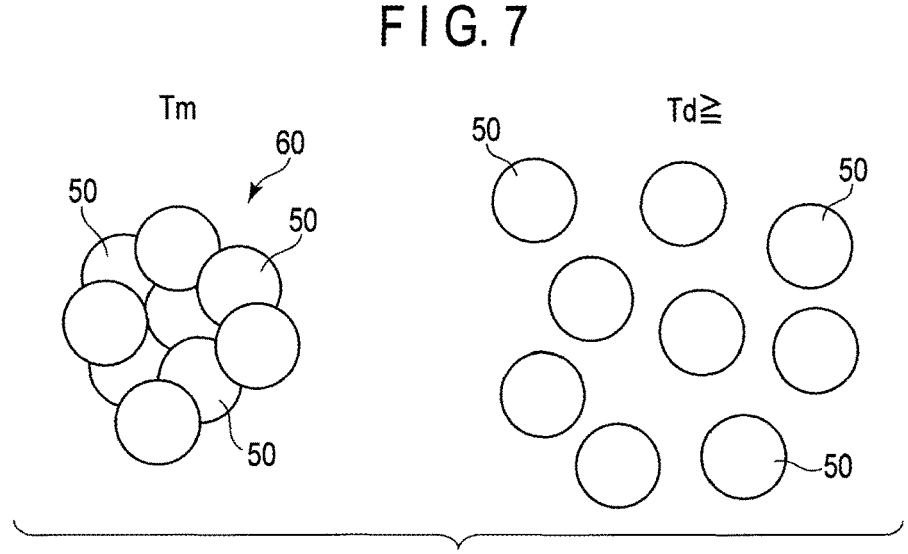
FIG. 8A is a view showing the reaction between a target substance and the component contained in the reagent of the inspection item according to the embodiment.

As shown in FIG. 8A, the primary reactants 50 aggregate at the measurement temperature Tm and form an aggregate 60 in the solution mixture. The solution mixture contains a specimen including no target substance A, the first reagent of the inspection item A1, and the second reagent of the inspection item A1. The primary reactants 50 disperse at a temperature equal to or lower than the dispersion temperature Td (for example, 32 degree Celsius) lower than the measurement temperature Tm.

Figure 8B:
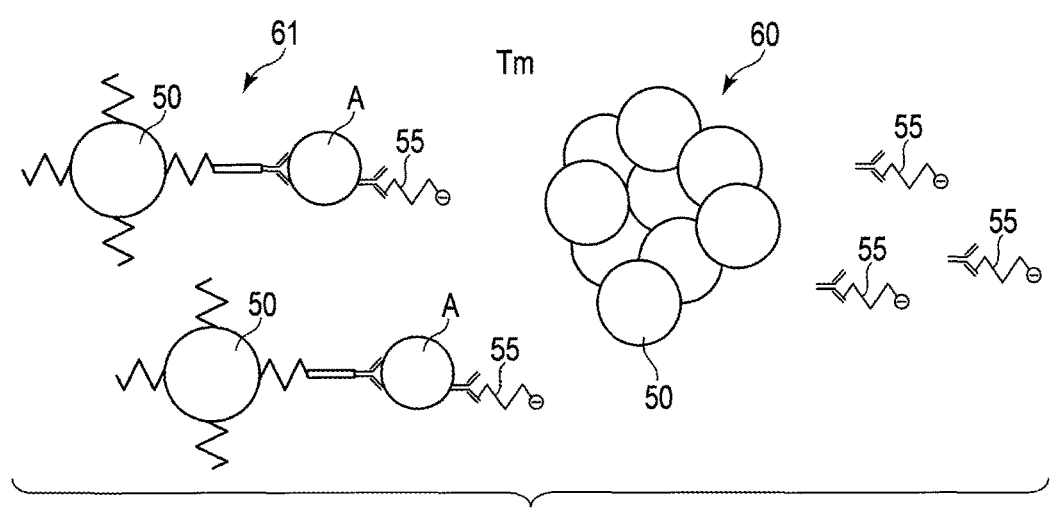
FIG. 8B is a view showing the reaction between the target substance and the component contained in the reagent of the inspection item according to the embodiment.

The secondary reactant 55 contains a second antibody 56 that reacts with and binds to the target substance A, and a charged substance 57 having a negative charge and bound to the second antibody 56. As shown in FIG. 8B, the secondary reactant 55 prevents aggregation of a bound body 61 formed by binding to the target substance A together with the primary reactant 50 in the solution mixture including the specimen including the target substance A and the first and second reagents of the inspection item A1 at the measurement temperature Tm.

When the charged substance 57 of the secondary reactant 55 bound to the target substance A is located near the thermoresponsive polymer 52 of the primary reactant 50, the aggregation of the bound body 61 is impeded.

Excess quantities of the primary reactants 50 and the secondary reactants 55 are contained in the second reagent. For this reason, as shown in FIG. 8B, the target substance A and the primary reactants 50 and the secondary reactants 55 in quantities corresponding to the target substance A bind in the solution mixture containing the specimen containing the target substance A and the first and second reagents of the inspection item A1 at the measurement temperature Tm. With this reaction, the bound bodies 61 are formed. The surplus primary reactants 50 form the aggregate 60. The bound bodies 61 and the surplus secondary reactants 55 disperse.

The action of the automatic analyzer 100 will be described next.

In the analysis section 10, the reagent containers 13 storing the first reagent of the target substance A are held by the reagent rack 14 in the first reagent storage 15. The reagent containers 13 storing the second reagent are held by the reagent rack 14 in the second reagent storage 16.

For example, the specimen container 11 storing a test specimen such as a blood serum or a blood plasma is placed on the sample table 12 of the analysis section 10, and the operation section 98 gives an instruction to start measurement to analyze the target substance A, the automatic analyzer 100 starts the operation.

The sample dispensing probe 19 sucks up the test specimen from the specimen container 11 placed on the sample table 12, and discharges it to the reaction vessel 171 of the reaction section 17. This operation is dispensing. The first reagent dispensing probe 21 sucks up the first reagent of the inspection item A1, which is kept cool in the first reagent storage 15, from the reagent container 13, and discharges it to the reaction vessel 171 in which the test specimen is dispensed.

The first stirrer 23 stirs the solution mixture in the reaction vessel 171 in which the test specimen and the first reagent are dispensed. The second reagent dispensing probe 25 sucks up the second reagent of the inspection item A1, which is kept cool in the second reagent storage 16, from the reagent container 13, and discharges it to the reaction vessel 171 in which the test specimen and the first reagent is dispensed.

The thermostat section 29 heats the solution mixture of the test specimen, the first reagent, and the second reagent in the reaction vessel 171 up to the measurement temperature Tm. The second stirrer 27 stirs the solution mixture of the test specimen, the first reagent, and the second reagent in the reaction vessel 171. The measuring section 30 irradiates the reaction vessel 171 with light and detects the light that has passed through the stirred solution mixture, thereby performing measurement.

Figure 9:
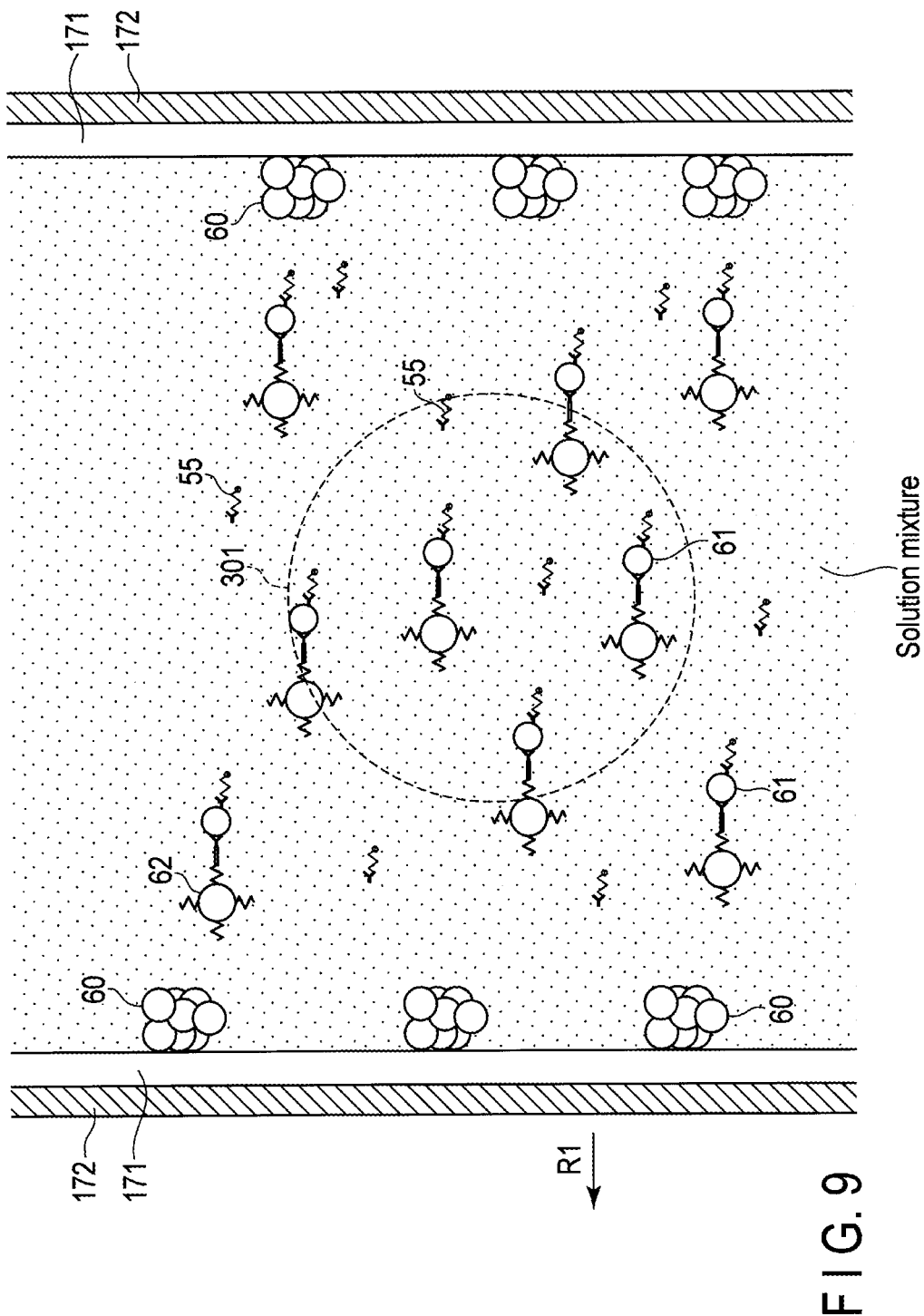
FIG. 9 is a view showing the interior of the reaction vessel storing a solution mixture heated to a measurement temperature and the magnets arranged on the reaction vessel according to the embodiment.

FIG. 9 is a view showing the interior of the reaction vessel 171 storing the solution mixture heated to the measurement temperature Tm and the magnets 172 arranged on the reaction vessel 171. In the solution mixture heated to the measurement temperature Tm, the bound bodies 61 of the target substance A contained in the test specimen and the primary reactants 50 and the secondary reactants 55 contained in the second reagent disperse. The surplus secondary reactants 55 also disperse. The surplus primary reactants 50 form the aggregates 60. Since the magnetic particles 51 are dense, the aggregates 60 are attracted by the magnets 172 and attract to the inner surfaces of the first and second side walls of the reaction vessel 171.

The measuring section 30 detects the light that passes through an optical path 301 in the solution mixture at a timing to avoid the vicinity of the inner surfaces of the first and second side walls of the reaction vessel 171 that moves across the measurement position, and generates test data. Here, the aggregates 60 are attracted by the magnets 172 and attract to the inner surfaces of the first and second side walls of the reaction vessel 171. Hence, the light that has passed among the dispersed secondary reactants 55 and bound bodies 61 in a region of the optical path 301 including no aggregates 60 is detected. As the concentration of the target substance A rises, the number of dispersed bound bodies 61 increases, and the turbidity rises. Hence, the light transmittance lowers.

Note that the light that has passed among the aggregates 60, the secondary reactants 55, and the bound bodies 61 included in the region of the optical path 301 may be detected when the aggregates 60 are moving toward the magnets 172.

The data processing section 92 generates the analysis data of the inspection item A1 from the test data generated by the measuring section 30. The output section 95 prints and displays the analysis data of the inspection item A1 generated by the data processing section 92.

The first cleaning nozzle 33 of the cleaning section 31 drains the solution mixture from the reaction vessel 171 that has undergone the measurement in the measuring section 30 and stopped at the first cleaning position Wi, and cleans the reaction vessel 171. After draining the solution mixture at the first cleaning position W1, the second cleaning nozzle 34 cleans the reaction vessel 171 that has stopped at the second cleaning position W2 using the first cleaning fluid cooled by the cooling section 48.

FIG. 10A shows the state in the reaction vessel 171 cleaned by the first cleaning nozzle 33. FIG. 10B shows the state in the reaction vessel 171 cleaned by the second cleaning nozzle 34.

When the solution mixture is sucked by the first cleaning nozzle 33 and drained from the reaction vessel 171, the aggregates 60 attracted by the magnets 172 and attracted to the inner surfaces of the first and second side walls of the reaction vessel 171 appear, as shown in FIG. 10A.

The second cleaning nozzle 34 has a discharge port and a suction port. The first cleaning fluid cooled to the cleaning temperature Tw is discharged from the discharge port by the first supply pump 41 of the supply section 40. The first cleaning fluid discharged from the discharge port is sucked from the suction port.

At this time of cleaning, the lower end of the second cleaning nozzle 34 stops at a position close to the bottom surface of the reaction vessel 171. In this state, the discharge port is located above the liquid level of the solution mixture in the reaction vessel 171. The discharge port discharges the first cleaning fluid toward the inner surfaces of the reaction vessel 171 to which the aggregates 60 are attracted.

The aggregates 60 attracted to the inner surfaces of the reaction vessel 171 are cooled by the first cleaning fluid to a temperature equal to or lower than the dispersion temperature Td and disperse. Since this makes the magnetic particles 51 sparse, the attracting force of the magnets 172 to the inner surfaces of the reaction vessel 171 weakens. Hence, the aggregates 60 evenly disperse in the first cleaning fluid. The suction port at the lower end of the second cleaning nozzle 34 sucks the first cleaning fluid including the primary reactants 50 dispersed from the aggregates 60.

In this embodiment, the cooling section 48 that cools the first cleaning fluid used to clean the reaction vessel 171 to the cleaning temperature Tw is provided. The first cleaning fluid cooled to the cleaning temperature Tw is discharged from the second cleaning nozzle 34 into the reaction vessel 171 that is held at the measurement temperature Tm by the thermostat section 29 even after the solution mixture is drained. Then, the aggregates 60 attracted to the inner surfaces of the reaction vessel 171 by the magnetic force of the magnets 172 disperse up to the primary reactants 50 due to the decrease in the temperature. The primary reactants 50 are drained from the reaction vessel 171.

Note that the plate-shaped magnets 172 arranged on the reaction vessel 171 of the reaction section 17 can be replaced with an annular magnet. In this case, the annular magnet, except the potion at the second cleaning position W2, may be arranged on at least one of the outer side surface and the inner side surface of the constant temperature oven 292 in the thermostat section 29.

According to the arrangement of this case, the aggregates 60 attracted to the inner surfaces of the reaction vessel 171 can be released from the magnetic force at the second cleaning position W2. It is therefore possible to raise the degree of dispersion of the aggregates 60 and drain them from the reaction vessel 171.

The third cleaning nozzle 35 discharges and sucks the second cleaning fluid into and from the reaction vessel 171 that has stopped at the third cleaning position W3 after the cleaning by the second cleaning nozzle 34, thereby further cleaning the reaction vessel 171.

The fourth cleaning nozzle 36 discharges and sucks the third cleaning fluid into and from the reaction vessel 171 that has stopped at the fourth cleaning position W4 after the cleaning by the third cleaning nozzle 35, thereby further cleaning the reaction vessel 171.

The fifth cleaning nozzle 37 discharges and sucks the first cleaning fluid into and from the reaction vessel 171 that has stopped at the fifth cleaning position W5 after the cleaning by the fourth cleaning nozzle 36, thereby further cleaning the reaction vessel 171. The reaction vessel 171 that has undergone the cleaning by the fifth cleaning nozzle 37 is moved to another location and used for the next measurement.

As described above, the interior of the reaction vessel 171 from which the aggregates 60 are removed at the second cleaning position W2 is cleaned using the second cleaning fluid and the third cleaning fluid which are different from the first cleaning fluid. This makes it possible to remove contaminants such as proteins unremovable by the first cleaning fluid from the reaction vessel 171.

Another example of cleaning of the reaction vessel 171 in the reaction section 17 will be described next. In this example, cleaning is performed, for example, before inspection, after inspection, or periodically.

First, the automatic analyzer 100 holds a cleaning container that has the same shape as the reagent container 13 and stores the first cleaning fluid in, for example, the reagent rack 14 in the first reagent storage 15. When given an instruction to start cleaning using the operation section 98, the automatic analyzer 100 starts the cleaning operation. Then, the heating device 296 in the heater 295 of the thermostat section 29 stops heating. After the heating device 296 stops, the drain pump 294 drains the heating medium 291 from the constant temperature oven 292.

After the heating medium 291 is drained from the constant temperature oven 292, the first reagent dispensing probe 21 sucks up, from the cleaning container, the first cleaning fluid kept at the cold temperature Tr in the first reagent storage 15, and discharges it into the reaction vessel 171, as shown in FIG. 11A.

That is, in this embodiment, the automatic analyzer 100 discharges the first cleaning fluid at the cold temperature Tr into the reaction vessel 171 whose temperature is lower than the measurement temperature Tm after the heating medium 291 is drained from the constant temperature oven 292.

Since the internal temperature of the reaction vessel 171 thus lowers, the aggregates 60 remaining on the inner surfaces of the reaction vessel 171 can be dispersed up to the primary reactants 50.

As shown in FIG. 11B, the first stirrer 23 stirs the first cleaning fluid in the reaction vessel 171 discharged from the first reagent dispensing probe 21. When the first cleaning fluid discharged into the reaction vessel 171 is stirred, the primary reactants 50 dispersed near the inner surfaces of the reaction vessel 171 can evenly be dispersed. After that, the reaction vessel 171 stops at the first cleaning position W1.

The first cleaning nozzle 33 drains the first cleaning fluid from the reaction vessel 171 that has stopped at the first cleaning position W1 and cleans the interior of the reaction vessel 171. After that, the reaction vessel 171 stops at the second cleaning position W2. The second cleaning nozzle 34 cleans the reaction vessel 171 that has stopped at the second cleaning position W2 using the first cleaning fluid cooled by the cooling section 48.

That is, in this embodiment, the automatic analyzer 100 drains the stirred first cleaning fluid from the reaction vessel 171, and then, causes the second cleaning nozzle 34 to discharge the first cleaning fluid at the cleaning temperature Tw. By cleaning using the first cleaning fluid cooled up to the cleaning temperature Tw, the inner surfaces of the reaction vessel 171 with the aggregates 60 attracted can be cleaned more powerfully. After cleaned by the second cleaning nozzle 34, the reaction vessel 171 stops at the third cleaning position W3.

The third cleaning nozzle 35 cleans the reaction vessel 171 that has stopped at the third cleaning position W3 using the second cleaning fluid. After cleaned by the third cleaning nozzle 35, the reaction vessel 171 stops at the fourth cleaning position W4.

The fourth cleaning nozzle 36 cleans the reaction vessel 171 that has stopped at the fourth cleaning position W4 using the third cleaning fluid. After cleaned by the fourth cleaning nozzle 36, the reaction vessel 171 stops at the fifth cleaning position W5.

The fifth cleaning nozzle 37 cleans the reaction vessel 171 that has stopped at the fifth cleaning position W5 using the first cleaning fluid. When all the processes of cleaning the interior of the reaction vessel 171 using the first reagent dispensing probe 21, the first stirrer 23, the first cleaning nozzle 33, the second cleaning nozzle 34, the third cleaning nozzle 35, the fourth cleaning nozzle 36, and the fifth cleaning nozzle 37 are completed, the automatic analyzer 100 ends the cleaning operation.

As described above, the automatic analyzer 100 according to this embodiment includes the cooling section 48. The cooling section 48 cools the first cleaning fluid used to clean the reaction vessel 171 up to the cleaning temperature Tw. The internal temperature of the reaction vessel 171 remains at the measurement temperature Tm even after the solution mixture is drained. However, when the first cleaning fluid at the cleaning temperature Tw is discharged from the second cleaning nozzle 34 into the reaction vessel 171, the internal temperature of the reaction vessel 171 lowers. This weakens the magnetic force of the magnetic particles 51, and the aggregates 60 attracted to the inner surfaces of the reaction vessel 171 by the magnetic force of the magnets 172 disperse up to the primary reactants 50. Hence, the aggregates 60 attracted to the inner surfaces of the reaction vessel 171 can easily be removed.

When the heating medium 291 is drained from the constant temperature oven 292, the internal temperature of the reaction vessel 171 becomes lower than the measurement temperature Tm. When the first cleaning fluid at the cold temperature Tr is discharged into the reaction vessel 171 in this state, the internal temperature of the reaction vessel 171 further lowers. Hence, and the aggregates 60 remaining on the inner surfaces of the reaction vessel 171 can further disperse up to the primary reactants 50.

The primary reactants 50 dispersed near the inner surfaces of the reaction vessel 171 can evenly be dispersed even by stirring the first cleaning fluid discharged into the reaction vessel 171. In this state, the automatic analyzer 100 drains the stirred first cleaning fluid in the reaction vessel 171, and causes the second cleaning nozzle 34 to discharge the first cleaning fluid at the cleaning temperature Tw. By cleaning the reaction vessel 171 using the discharged first cleaning fluid, the inner surfaces of the reaction vessel 171 after attraction of the aggregates 60 can be cleaned more powerfully.

It is therefore possible to reliably remove contaminations on the inner surfaces of the reaction vessel 171 and prevent residual contaminations from adversely affecting measurement.

Note that the present invention is not limited to the above-described embodiment. For example, the automatic analyzer according to the embodiment is usable not only for an immunoassay based on an antigen-antibody reaction but also for a biochemical inspection. That is, the common analysis section 10 can execute immunoassay items and biochemical inspection items. In this case, since the same reaction vessels 171 are shared for the immunoassay and the biochemical inspection, it is more important to sufficiently clean the reaction vessels 171. The automatic analyzer according to the embodiment is also usable for an infection inspection in addition to the immunoassay and the biochemical inspection.

Each of the functions of the described embodiments may be implemented by one or more processing circuits. A processing circuit includes a programmed processor, as a processor includes circuitry. A processing circuit also includes devices such as an application specific integrated circuit (ASIC) and conventional circuit components arranged to perform the recited functions.

What is claimed is:

1. An automatic analyzer comprising:
a storage configured to keep a reagent container storing a reagent containing thermoresponsive polymers and a cleaning fluid container storing a cleaning fluid;
a cooler cooling the reagent container and the cleaning fluid container in the storage, and the cooler cools the cleaning fluid in the cleaning fluid container to a temperature at which the thermoresponsive polymers disperse;
a specimen dispenser dispensing a specimen into a reaction vessel;
a reagent dispenser dispensing the reagent into the reaction vessel;
a thermostat unit heating a solution mixture, of the specimen and the reagent in the reaction vessel to a temperature at which the thermoresponsive polymers aggregate;
a measurement unit measuring the solution mixture in the reaction vessel;
a magnet arranged on an outer surface of the reaction vessel or near the outer surface of the reaction vessel;
a cleaner discharging the cleaning fluid cooled to the temperature of the storage toward the reaction vessel from which the solution mixture has been drained, thereby dispersing the thermoresponsive polymers in the reaction vessel, and cleaning the reaction vessel; and
wherein the reagent dispenser dispenses a reagent containing: a primary reactant containing a magnetic particle and the thermoresponsive polymer that aggregates at a temperature of the heated solution mixture and disperses at a temperature of the cooled cleaning fluid; and
a secondary reactant configured to prevent aggregation of a bound body formed by-binding to the target substance together with the primary reactant at the first temperature of the heated solution mixture in the solution mixture containing the target substance, and
the magnet attracts an aggregate formed by aggregation of the primary' reactants in surplus in the solution mixture containing the target substance in the reaction vessel heated by the thermostat unit.

2. The automatic analyzer of claim 1, wherein an inspection item to be analyzed includes a biochemical inspection item and an immunoassay item.

3. The automatic analyzer of claim 1, wherein
the cleaner sucks the discharged cleaning fluid, thereby cleaning the reaction vessel.

4. The automatic analyzer of claim 1, wherein the thermostat unit comprises:
a constant temperature oven storing a heating medium used to heat the reaction vessel and the solution mixture in the reaction vessel to a measurement temperature; and
a drain pump draining the heating medium from the constant temperature oven, and the cleaner cleans the reaction vessel using the cleaning fluid cooled to the temperature of the reagent container after the heating medium is drained from the constant temperature oven.

5. The automatic analyzer of claim 1, further comprising:
a stirrer stirring the cleaning fluid in the reaction vessel discharged from the cleaner.

6. The automatic analyzer of claim 5, wherein the magnet attracts an aggregate formed by aggregation of the primary reactants in surplus in the solution mixture containing the target substance in the reaction vessel heated by the heating medium.

7. The automatic analyzer of claim 1, wherein the cleaning fluid is ion exchanged water or distilled water.

* * * * *